United States Patent [19]

Matsumoto et al.

[11] 4,359,578
[45] Nov. 16, 1982

[54] NAPHTHYRIDINE DERIVATIVES AND SALTS THEREOF USEFUL AS ANTIBACTERIAL AGENTS

[75] Inventors: Jun-ichi Matsumoto, Takatsuki; Yoshiyuki Takase, Amagasaki; Yoshiro Nishimura, Neyagawa, all of Japan

[73] Assignees: Dainippon Pharmaceutical Co., Ltd., Osaka, Japan; Laboratoire Roger Bellon, Neuilly sur Seine, France

[21] Appl. No.: 68,966

[22] Filed: Aug. 23, 1979

[30] Foreign Application Priority Data

Aug. 25, 1978 [JP] Japan ................................. 53/104235
Dec. 20, 1978 [JP] Japan ................................. 157939
Dec. 29, 1978 [JP] Japan ................................. 53/162095

[51] Int. Cl.³ .................. C07D 471/04; A61K 31/495
[52] U.S. Cl. ..................................... 544/362; 424/250; 544/16; 544/127; 544/279; 544/363; 544/364; 546/123; 546/312
[58] Field of Search ............................................. 544/362

[56] References Cited

U.S. PATENT DOCUMENTS

| | | | |
|---|---|---|---|
| 3,149,104 | 9/1964 | Lesher et al. | 544/362 |
| 3,849,421 | 11/1974 | Nakagome et al. | 544/362 |
| 4,017,622 | 4/1977 | Minami et al. | 544/362 |
| 4,146,719 | 3/1979 | Irikura | 424/250 |

FOREIGN PATENT DOCUMENTS 2939786 4/1980 Fed. Rep. of Germany.
55-47658 4/1980 Japan.
2034698 6/1980 United Kingdom.

Primary Examiner—Donald G. Daus
Assistant Examiner—James H. Turnipseed
Attorney, Agent, or Firm—Wenderoth, Lind & Ponack

[57] ABSTRACT

This invention relates to 1,8-naphthyridine compounds of the formula

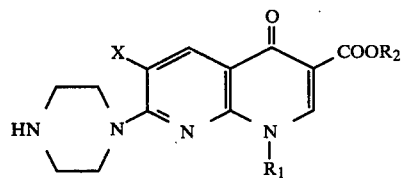

wherein
X is a halogen atom especially fluorine atom,
$R_1$ is an ethyl group or a vinyl group, and
$R_2$ is a hydrogen atom or a lower alkyl group, their salts and processes for the preparation of them.

The 1,8-naphthyridine compounds and their salts are useful as antibacterial agents and intermediates thereof.

4 Claims, No Drawings

NAPHTHYRIDINE DERIVATIVES AND SALTS THEREOF USEFUL AS ANTIBACTERIAL AGENTS

This invention relates to novel naphthyridine derivatives having high antibacterial activities, their intermediates, processes for preparing said novel compounds, and also to their use.

The present invention provides compounds of the following formula

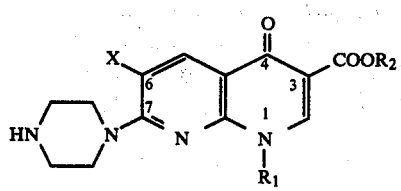

wherein X is a halogen atom, especially a fluorine atom, $R_1$ is an ethyl or vinyl group, and $R_2$ is a hydrogen atom or a lower alkyl group; and nontoxic salts thereof.

In the present specification and appended claims, the term "lower alkyl group" either in itself or as part of other groups denotes an alkyl group containing 1 to 6 carbon atoms.

The salts of the naphthyridine compounds (I) are formed between the naphthyridine compounds (I) and acids or bases. The acids may be various inorganic and organic acids, and examples of suitable acids are hydrochloric acid, acetic acid, lactic acid, succinic acid, lactobionic acid, and methanesulfonic acid. The bases may be any inorganic or organic bases capable of forming salts with the carboxyl group of the compounds (I), and examples of suitable bases are metal hydroxides such as sodium or potassium hydroxide, and metal carbonates such as sodium or potassium carbonate.

Especially preferred salts of the compounds (I) are the hydrochlorides or methanesulfonates.

Depending upon the conditions, the naphthyridine compounds (I) may form as hydrates. These hydrates are also embraced by the naphthyridine compounds of the present invention which are represented by formula (I).

It is an object of this invention to provide novel naphthyridine compounds having high antibacterial activities against Gram-positive bacteria and Gram-negative bacteria including *Pseudomonas aeruginosa*, and processes for preparing these novel compounds.

Another object of this invention is to provide a pharmaceutical composition containing such a novel naphthyridine compound.

Still another object of this invention is to provide a pharmaceutical use of these novel compounds.

These and other objects of this invention become apparent from the following description.

Typical examples of the novel compounds of this invention are given below with their structural formulae.

1-Ethyl-6-fluoro-1,4-dihydro-4-oxo-7-(1-piperazinyl)-1,8-naphthyridine-3-carboxylic acid (compound 1) of the following formula, and its nontoxic pharmaceutically acceptable salts.

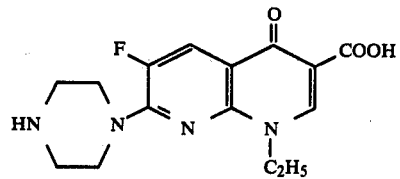

Ethyl 1-ethyl-6-fluoro-1,4-dihydro-4-oxo-7-(1-piperazinyl)-1,8-naphthyridine-3-carboxylate (the ethyl ester of compound 1) of the following formula, and its nontoxic pharmaceutically acceptable salts.

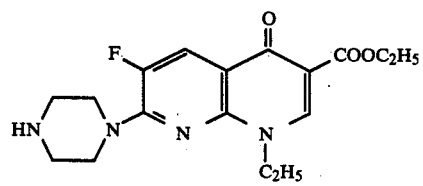

6-Fluoro-1,4-dihydro-4-oxo-7-(1-piperazinyl)-1-vinyl-1,8-naphthyridine-3-carboxylic acid (compound 2) of the following formula, and its nontoxic pharmaceutically acceptable salts.

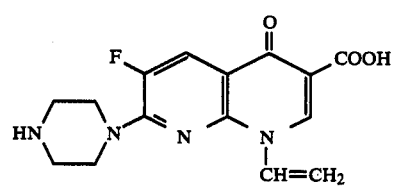

Ethyl 6-fluoro-1,4-dihydro-4-oxo-7-(1-piperazinyl)-1-vinyl-1,8-naphthyridine-3-carboxylate (the ethyl ester of compound 2) of the following formula, and its nontoxic pharmaceutically acceptable salts.

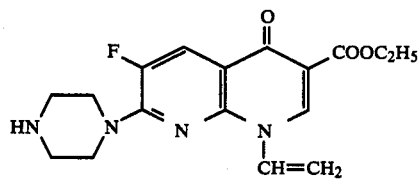

6-Chloro-1-ethyl-1,4-dihydro-4-oxo-7-(1-piperazinyl)-1,8-naphthyridine-3-carboxylic acid (compound 3) of the following formula, and its nontoxic pharmaceutically acceptable salts.

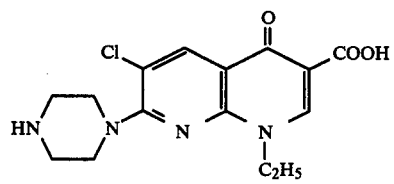

6-Chloro-1,4-dihydro-4-oxo-7-(1-piperazinyl)-1-vinyl-1,8-naphthyridine-3-carboxylic acid (compound 4) of the following formula, and its nontoxic pharmaceutically acceptable salts.

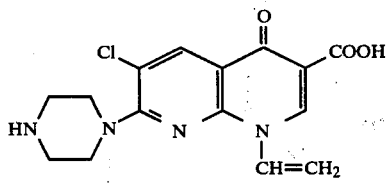

Among the naphthyridine compounds of this invention, compound 1 and its salts are most valuable as antibacterial agents. As shown in Tables I to VI given hereinbelow, the compound 1 and its salts exhibit very high antibacterial activities both in vitro and in vivo tests against Gram-positive bacteria and Gram-negative bacteria including *Pseudomonas aeruginosa*. Since they have extremely low toxicity, they are useful for the treatment of not only urinary tract infections caused by various Gram-positive and Gram-negative bacteria but also systemic infections caused by these bacteria.

Next to the compound 1 and its salts, compound 2 and its salts are valuable as antibacterial agents. The lower alkyl esters of compounds 1 and 2 exhibit fairly high antibacterial activities in vivo. These esters are useful not only as antibacterial agents but also as intermediates for the synthesis of compounds 1 and 2.

As structurally similar compounds to compounds 1 and 2 of this invention, U.S. Pat. No. 4,017,622 discloses piperazine derivatives of the following formula, and their salts.

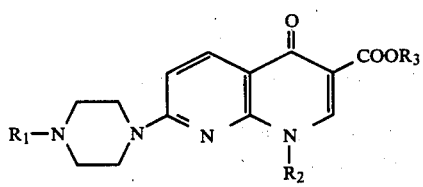

In the above formula, $R_1$ is a hydrogen atom, an alkyl group having 1 to 4 carbon atoms, a benzyl group or an acetyl group; $R_2$ is a hydrogen atom, an alkyl group having 1 to 4 carbon atoms, a benzyl group or a vinyl group; and $R_3$ is a hydrogen atom or an alkyl group having 1 to 6 carbon atoms.

As is clearly seen from the above formula, the 1,8-naphthydridine derivatives disclosed in U.S. Pat. No. 4,017,622 have no substituent at the 6-position of the naphthyridine nucleus.

Investigations of the present invention have shown that as shown in Examples A and B given hereinbelow, the compounds of this invention have much better antibacterial activities against Gram-negative bacteria including *Pseudomonas aeruginosa* as well as Gram-positive bacteria than the 1,8-naphthyridine derivatives disclosed in the above U.S. patent.

Japanese Laid-Open Patent Publication No. 83590/77 [the abstract of which is disclosed in Central Patents Index published by Derwent Publications Ltd., under Accession No. (to be abbreviated Der. No.) 60389Y/34] discloses 6-nitro-1,8-naphthyridine derivatives of the following formula

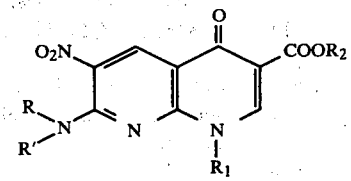

In the above formula, —N(R)(R') is a member selected from the group of amino, substituted anilino, alkylamino, (cyclo)alkylamino, dialkylaminoalkylamino, hydroxyalkylamino, dialkylamino, alkylallylamino, alkylcycloalkylamino, dihydroxyalkylamino, pyrrolidino, piperidino, morpholino, and piperazino, and each of $R_1$ and $R_2$ is lower alkyl.

The Japanese Publication, however, only states that these compounds have anti-trichomonal activity. Thus, it does not relate to antibacterial agents as does the present invention.

Summary of the Proceedings of the 98th Annual Meeting of Pharmaceutical Society of Japan, page 233 (published Mar. 10, 1978) reports that compounds of the following formula in which $R_1$ is an ethyl group or a group corresponding to it, $R_2$ is hydrogen, $R_3$ and $R_5$ are electron-attracting groups and $R_4$ is an electron-donating group have been found to have strong activity.

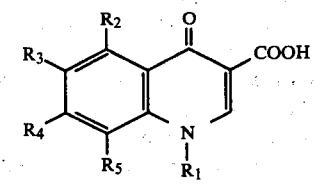

This publication states that compounds of the above formula in which $R_3$ and $R_5$ are chlorine or fluorine and $R_4$ is piperazino or substituted piperazino have been studied for the relation between their structures and activities, and compounds of the formula in which $R_1$ is ethyl, $R_2$ is hydrogen, $R_3$ or $R_5$ is chlorine or fluorine, and $R_4$ is piperazino have been found to exhibit stronger antibacterial activities than nalidixic acid.

U.S. Pat. No. 4,146,719 corresponding to Belgian Pat. No. 863,429 discloses the quinoline derivative of the following formula (to be sometimes referred to as compound D)

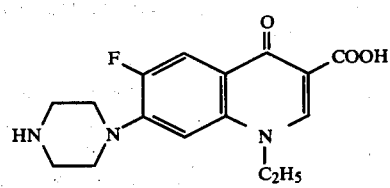

Japanese Laid-Open Patent Publication No. 65887/78 (the abstract of which is disclosed in Der No. 52436A/29) discloses the quinoline derivative of the following formula (to be sometimes referred to as compound C).

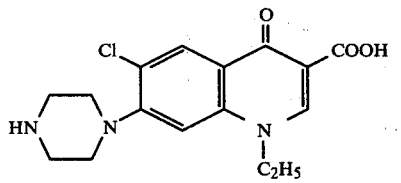

Investigations of the present inventors have shown that as shown in Tables II and III given hereinbelow, compounds 1 and 2 of the invention have much better antibacterial activities against Gram-negative bacteria including *Pseudomonas aeruginosa* than quinoline derivatives such as the compounds C and D.

The compounds of formula [I] can be synthesized, for example, by the following processes (1) and (2).

Process (1): Alkylation

Of the compounds of formula [I], those in which $R_1$ is an ethyl group, that is, compounds of the following formula,

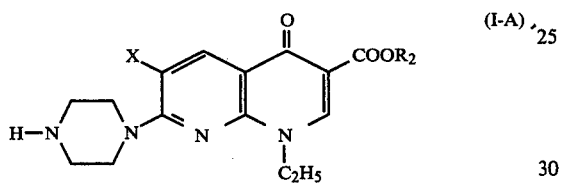

wherein X and $R_2$ are the same as defined in formula [I], are obtained by reacting a compound of the following formula,

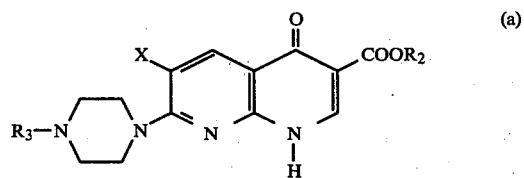

wherein $R_2$ and X are the same as defined in the formula [I], and $R_3$ is a hydrogen atom or an acyl group, with an ethylating agent. Examples of the acyl group as $R_3$ are formyl, acetyl, trifluoroacetyl, benzyloxycarbonyl, t-butoxycarbonyl, p-methoxybenzyloxycarbonyl, vinyloxycarbonyl, ethoxycarbonyl, and β-(p-toluenesulfonyl)ethoxycarbonyl. Any known ethylating agents can be used. Specific examples include ethyl halides such as ethyl iodide and ethyl esters such as diethyl sulfate, ethyl p-toluenesulfonate, or triethyl phosphate.

This reaction is generally carried out by reacting the compound (a) with a stoichiometric amount of the ethylating agent in an inert solvent at an elevated temperature of, say, 25° C. to 150° C. When $R_3$ is an acyl group, the ethylating agent may be used in excess.

Examples of the solvent are ethanol, dioxane, methyl cellosolve, dimethylformamide, dimethyl sulfoxide, and water. The reaction is accelerated by adding an acid-acceptor, for example a base such as an alkali metal carbonate, an alkali metal hydroxide, an alkali metal alkoxide, sodium hydride, pyridine, triethylamine, and benzyltrimethylammonium hydroxide.

When this reaction results in a product in which $R_3$ is an acyl, it is hydrolyzed in a customary manner to form the desired product of formula ([I-A].

Process (2): Vinylation

Of the compounds of formula [I], those in which $R_1$ is a vinyl group, that is, compounds of the following formula

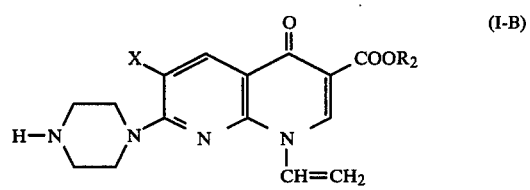

wherein $R_2$ and X are the same as defined in formula [I] above, can be obtained by heating a compound of the following formula

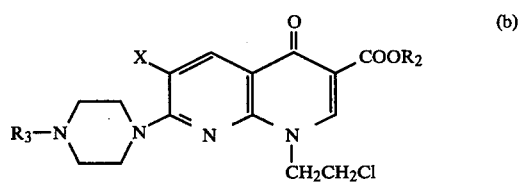

wherein X, $R_2$ and $R_3$ are the same as defined above.

The reaction is carried out by heating the compound (b) in the presence of a catalyst such as a base. Examples of the catalyst are ordinary bases such as potassium bicarbonate, alkali metal hydroxides, alkali metal carbonates, metal hydrides such as sodium hydride, alkali metal alkoxides such as sodium ethoxide, sodium methoxide or potassium tert.-butoxide, pyridine, collidine, and benzyltrimethylammonium hydroxide.

The reaction temperature is usually 50° C. to 270° C. The reaction proceeds in the absence of solvent, but preferably, it is carried out in an inert solvent. Examples of the solvents are water, alcohols, dimethylformamide, dimethylsulfoxide, diethyl ether, benzene, dioxane, tetrahydrofuran, and pyridine.

When this reaction results in a product in which $R_3$ is acyl, it is hydrolyzed in a customary manner to obtain the desired product of formula [I-B]. The starting compounds (a) and (b) wherein $R_2$ is an ethyl group can be obtained as schematically shown below.

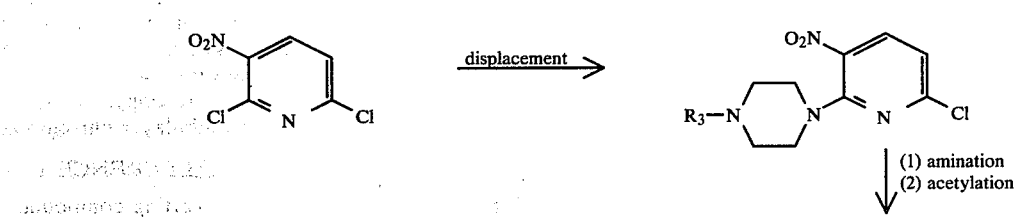

-continued

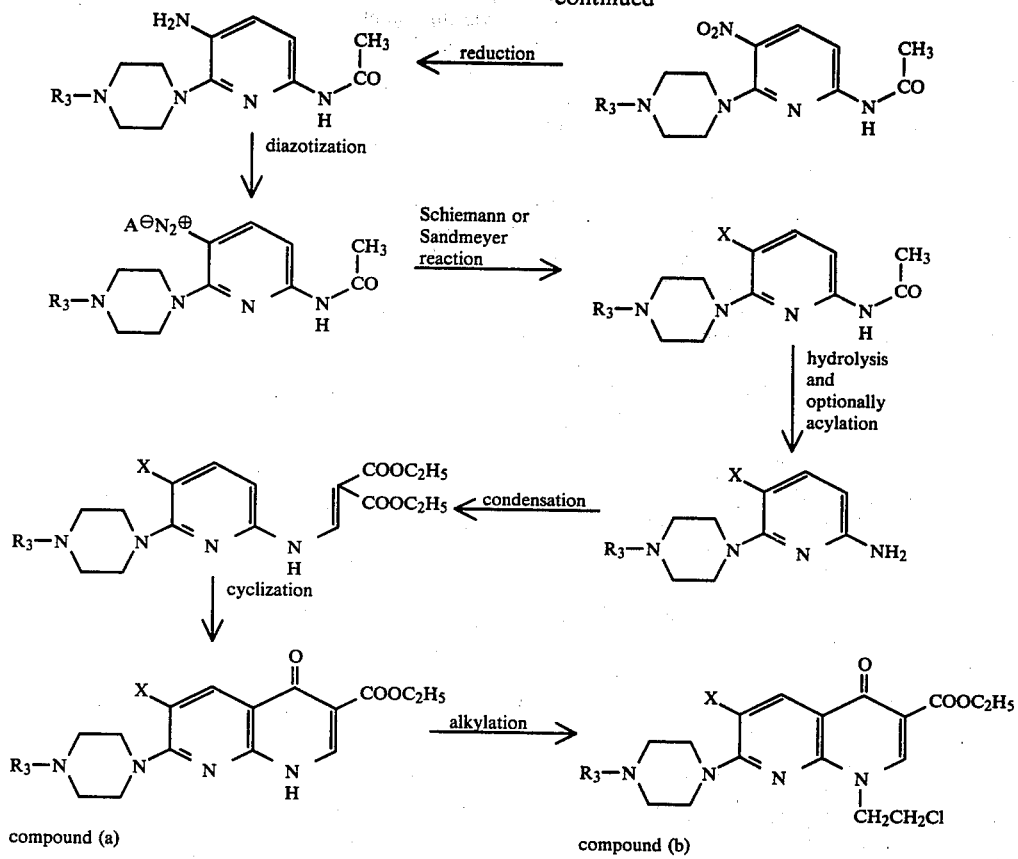

compound (a)   compound (b)

The compounds of the present invention prepared in the above process can be isolated and purified by usual methods. The compounds [I] can be obtained in the free state or in the form of a salt depending upon the selection of the starting materials and the reaction conditions. The compounds [I] can be converted to pharmaceutically acceptable salts by treating them with an acid or a base. The acid may be a variety of organic and inorganic acids, examples of which are hydrochloric acid, acetic acid, lactic acid, succinic acid, lactobionic acid, oxalic acid and methanesulfonic acid.

The novel 1,8-naphthyridine derivatives of this invention, as will be shown in Examples given hereinbelow, have excellent antibacterial activities and low toxicity. Accordingly, these compounds can be used as drugs for the treatment or prevention of bacterial infections of warm-blooded animals including man.

The dosage of the compound [I] or its salt of this invention in administration to man should be adjusted according to the age, body weight and condition of the patient, the administration route, the number of administrations, etc. Usually, the dosage for adults is 0.1 to 7 g/day, preferably 0.2 to 5 g/day.

The compounds of this invention may be used as medicines, for example, in the form of pharmaceutical preparations containing them in admixture with an organic or inorganic pharmaceutically acceptable solid or liquid adjuvants suitable for oral or topical administration.

Pharmaceutically acceptable adjuvants are substances that do not react with the compounds of this invention. Examples are water, gelatin, lactose, starch, cellulose (preferably, microcrystalline cellulose), carboxymethyl cellulose, methyl cellulose, sorbitol, magnesium stearate, talc, vegetable oils, benzyl alcohol, gums, propylene glycol, polyalkylene glycols, methylparaben and other known medicinal adjuvants. The pharmaceutical preparations may be powder, granules, tablets, ointments, suppositories, creams, capsules, etc. They may be sterilized, and/or contain assistants such as preserving, stabilizing or wetting agents. They may further contain other therapeutically valuable substances according to the purpose of medication.

The processes for producing the novel compounds [I] and their salts of the invention and their pharmacological activities are specifically illustrated below.

Referrences 1 and 2 show processes for the preparation of starting compounds.

Examples 1 to 6 illustrate processes for the preparation of the compounds [I] or their salts of this invention.

Reference 3 shows a process for preparation of a compound which is new, and is outside the scope of this invention as controls.

Examples A to G show the pharmacological activities of the compounds [I] and their salts of this invention in comparison with those of compounds which are outside the scope of this invention.

Examples H and J show the preparations of pharmaceuticals containing the compound [I] of this invention.

The compounds obtained in Examples and Reference Examples hereinbelow were identified by elemental analysis, mass spectroscopy, IR spectroscopy, NMR spectroscopy and thin-layer chromatography.

REFERENCE 1

Preparation of a starting compound of the formula

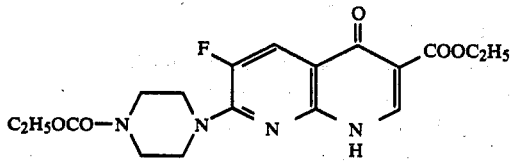

2,6-Dichloro-3-nitropyridine was reacted with N-ethoxycarbonylpiperazine to give 6-chloro-2-(4-ethoxycarbonyl-1-piperazinyl)-3-nitropyridine. The product, without purification, was heated with ethanolic ammonia in a sealed tube at 120°–125° C. to give 6-amino-2-(4-ethoxycarbonyl-1-piperazinyl)-3-nitropyridine (mp 132°–134° C.), which was treated with acetic anhydride in acetic acid to give 6-acetylamino-2-(4-ethoxycarbonyl-1-piperazinyl)-3-nitropyridine (mp 168°–169° C.). This compound was catalytically hydrogenated in the presence of 5% palladium-carbon in acetic acid to yield 3-amino-6-acetylamino-2-(4-ethoxycarbonyl-1-piperazinyl)pyridine. The obtained 3-amino derivative, without further purification, was dissolved in a mixture of ethanol and 42% tetrafluoroboric acid, and to this solution was added a solution of isoamyl nitrite in ethanol at below 0° C. with stirring. Twenty minutes later, ether was added to the solution. The resulting precipitate was collected by filtration and washed with a mixture of methanol and ether and then with chloroform to yield 6-acetylamino-2-(4-ethoxycarbonyl-1-piperazinyl)-3-pyridine diazonium tetrafluoroborate; mp 117°–117.5° C. (dec.).

A suspension of the diazonium salt in toluene was gradually heated and kept at 120° C. (bath temp.) for 30 minutes with stirring. After evaporation of the solvent under reduced pressure, the residue was made alkaline with 10% sodium carbonate and then extracted with chloroform. The chloroform extract was dried over anhydrous potassium carbonate. After evaporation of the solvent, the crystalline residue was recrystallized from ethyl acetate to give 6-acetylamino-2-(4-ethoxycarbonyl-1-piperazinyl)-3-fluoropyridine (mp 132°–133° C.). The 3-fluoro derivative was hydrolyzed with a mixture of 15% hydrochloric acid and methanol (1:2 v/v) to give 6-amino-2-(4-ethoxycarbonyl-1-piperazinyl)-3-fluoropyridine. This compound was treated with diethyl ethoxymethylenemalonate at 130°–140° C. to give N-[2-(4-ethoxycarbonyl-1-piperazinyl)-3-fluoro-6-pyridinyl]aminomethylenemalonate (mp 144°–145° C.) and then the product was cyclized by heating at 255° C. to give ethyl 7-(4-ethoxycarbonyl-1-piperazinyl)-6-fluoro-1,4-dihydro-4-oxo-1,8-naphthyridine-3-carboxylate (mp 279°–281° C.).

REFERENCE 2

Preparation of a starting compound of the formula

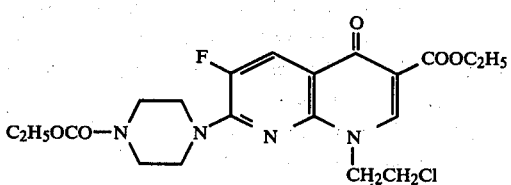

A mixture of ethyl 7-(4-ethoxycarbonyl-1-piperazinyl)-6-fluoro-1,4-dihydro-4-oxo-1,8-naphthyridine-3-carboxylate (10.5 g), dimethylformamide (100 ml), and potassium carbonate (7.4 g) was heated at 100° C. for 15 minutes. To the solution was added a solution of 10.1 g of ethylene bromohydrin in dimethylformamide (10 ml), and the mixture was heated at 100° C. for 45 minutes with stirring. After removal of the resulting inorganic substance by filtration, the filtrate was concentrated to dryness under reduced pressure. Water (80 ml) was added to the residue, and the resulting crystals were collected by filtration and recrystallized from ethanol to give 10.2 g of ethyl 7-(4-ethoxycarbonyl-1-piperazinyl)-6-fluoro-1-(2-hydroxyethyl)-1,4-dihydro-4-oxo-1,8-naphthyridine-3-carboxylate (mp 215°–217° C.). Thionyl chloride (5.0 g) was added to the solution of the resulting hydroxyethyl derivative (4.6 g) in chloroform (50 ml), and the mixture was refluxed under heating for 30 minutes. After cooling, the solution was treated with 30 ml of water and neutralized with a saturated sodium bicarbonate solution. The chloroform layer was separated, washed with water, and dried over anhydrous sodium sulfate. After removal of the solvent, the residue was chromatographed on silica gel with chloroform and the crystals resulting from the main fraction were recrystallized from ethyl acetate to give 4.7 g of ethyl 1-(2-chloroethyl)-7-(4-ethoxycarbonyl-1-piperazinyl)-6-fluoro-1,4-dihydro-4-oxo-1,8-naphthyridine-3-carboxylate (mp 143°–144° C.).

EXAMPLE 1

Preparation of compound 1 and acid addition salts thereof

Ethyl 7-(4-ethoxycarbonyl-1-piperazinyl)-6-fluoro-1,4-dihydro-4-oxo-1,8-naphthyridine-3-carboxylate was suspended in dimethylformamide (10 ml) and to the suspension was added potassium carbonate (0.53 g.). After the mixture was kept at 60° C. for 10 minutes with stirring, ethyl iodide (1.2 g) was added to the solution. The mixture was stirred for 2 hours at 60°–70° C. The reaction mixture was concentrated to dryness under reduced pressure, and water was added to the residue. After extraction with chloroform, the chloroform extract was dried over anhydrous potassium carbonate. After removal of the chloroform by distillation, the resulting precipitate was recrystallized from a mixture of dichloromethane and n-hexane to give 0.89 g of ethyl 1-ethyl-6-fluoro-1,4-dihydro-4-oxo-7-(4-ethoxycarbonyl-1-piperazinyl)-1,8-naphthyridine-3-carboxylate (mp 171°–173° C.). A mixture of the above ethyl ester (0.8 g), 10% sodium hydroxide (6 ml) and ethanol (2 ml) was refluxed by heating for 3 hours. After cooling, the solution was adjusted to pH 7.0–7.5 with 10% acetic acid. The precipitate was collected by filtration, washed with ethanol and recrystallized from a mixture of dimethylformamide and ethanol to give 0.57 g of 1-ethyl-6-fluoro-1,4-dihydro-4-oxo-7-(1-piperazinyl)-1,8-naphthyridine-3-carboxylic acid. m.p. 220°–224° C.

The carboxylic acid (0.2 g) thus obtained was dissolved in 5% hydrochloric acid, and the solution was concentrated to dryness under reduced pressure. The residue was crystallized from water to give a hydrochloride of the carboxylic acid (0.21 g). m.p. above 300° C. On the other hand, the above free carboxylic acid (0.2 g) was dissolved in 7% methanesulfonic acid solution under heating. After cooling, the precipitate was recrystallized from diluted methanol to give a methanesulfonic acid salt of the carboxylic acid (0.22 g), mp. above 300° C. (dec.).

The free carboxylic acid (1.0 g) was heated to dissolve in ethanol and then to the solution was added acetic acid (1.0 ml). After the mixture was cooled, the resulting crystals were collected and recrystallized from ethanol to give acetic acid salt of the carboxylic acid (0.93 g), m.p. 228°–229° C.

EXAMPLE 2

Preparation of compound 3 hydrochloride

6-Chloro-1-ethyl-1,4-dihydro-4-oxo-7-(1-piperazinyl)-1,8-naphthyridine-3-carboxylic acid hydrochloride (m.p. above 300° C.) was obtained from ethyl 6-chloro-7-(4-ethoxycarboxyl-1-piperazinyl)-1,4-dihydro-4-oxo-1,8-naphthyridine-3-carboxylate by the same procedure as described in Example 1.

EXAMPLE 3

Preparation of ethyl ester of compound 1

Ethyl 6-fluoro-1,4-dihydro-4-oxo-7-(4-trifluoroacetyl-1-piperazinyl)-1,8-naphthyridine-3-carboxylate was treated with ethyl iodide and potassium carbonate in dimethylformamide by the same procedure as described in Example 1 to form ethyl 1-ethyl-6-fluoro-1,4-dihydro-4-oxo-7-(4-trifluoroacetyl-1-piperazinyl)-1,8-naphthyridine-3-carboxylate. This product was hydrolyzed by treating with aqueous potassium carbonate in a mixture of chloroform and methanol to give ethyl 1-ethyl-6-fluoro-1,4-dihydro-4-oxo-7-(1-piperazinyl)-1,8-naphthyridine-3-carboxylate, m.p. 150°–151° C.

EXAMPLE 4

Preparation of propyl and butyl esters of compound 1

Propyl 1-ethyl-6-fluoro-1,4-dihydro-4-oxo-7-(1-piperazinyl)-1,8-naphthyridine-3-carboxylate (m.p. 133°–135° C.) and butyl 1-ethyl-6-fluoro-1,4-dihydro-4-oxo-7-(1-piperazinyl)-1,8-naphthyridine-3-carboxylate (m.p. 119°–120° C.) were obtained by the same procedure as described in Example 1.

EXAMPLE 5

Preparation of compound 2 and acid addition salts thereof

Ethyl 1-(2-chloroethyl)-7-(4-ethoxycarboxyl-1-piperazinyl)-6-fluoro-1,4-dihydro-4-oxo-1,8-naphthyridine-3-carboxylate (2.27 g) was dissolved in ethanol (15 ml) by heating, and to the solution was added a solution of potassium hydroxide (0.84 g) in ethanol (15 ml). The resulting solution was heated to reflux for 2 hours with stirring. The resulting crystals were collected by filtration and washed with ethanol. The crystals were then dissolved in 20 ml of water by heating, and the solution was adjusted to pH 4–5 with 10% acetic acid. The resulting crystals were collected by filtration, washed with ethanol and recrystallized from a mixture of ethanol and chloroform to give 1.74 g of 7-(4-ethoxycarbonyl-1-piperazinyl)-6-fluoro-1,4-dihydro-4-oxo-1-vinyl-1,8-naphthyridine-3-carboxylic acid (mp 246°–248° C.). Five percent sodium hydroxide solution (30 ml) was added to 1.5 g of 7-(4-ethoxycarbonyl-1-piperazinyl)-6-fluoro-1,4-dihydro-4-oxo-1-vinyl-1,8-naphthyridine-3-carboxylic acid. The mixture was heated to reflux for 5 hours with stirring. After cooling, the solution was adjusted to pH 7 with acetic acid. The resulting precipitate was collected by filtration. The precipitate was dissolved in aqueous 10% acetic acid under heating, and the solution was adjusted to pH 9 with ammonia solution. The resulting precipitate was collected by filtration to give 0.98 g of 6-fluoro-1,4-dihydro-4-oxo-7-(1-piperazinyl)-1-vinyl-1,8-naphthyridine-3-carboxylic acid, m.p. 256°–260° C.

The carboxylic acid (0.2 g) was mixed with a small amount of concentrated hydrochloric acid, and the resulting hydrochloride was collected by filtration. It was recrystallized from ethanol to give a hydrochloric acid salt of the carboxylic acid (0.21 g), m.p. 290° C. (dec.).

The above free carboxylic acid (0.2 g) was dissolved in 7% methanesulfonic acid solution under heating. After cooling, the precipitate was recrystallized from diluted ethanol to give a methanesulfonic acid salt of the carboxylic acid (0.20 g), m.p. 291°–293° C. (dec.).

EXAMPLE 6

Preparation of compound 4

To a solution of potassium carbonate (1.52 g) in ethanol (40 ml) which was kept at 90°–95° C., was added ethyl 7-(4-acetyl-piperazinyl)-6-chloro-1-(2-chloroethyl)-1,4-dihydro-4-oxo-1,8-naphthyridine-3-carboxylate (4.0 g) and the mixture was heated to reflux for 1.5 hours. After the mixture was cooled, the resulting potassium 7-(4-acetyl-1-piperazinyl)-6-chloro-1,4-dihydro-4-oxo-1-vinyl-1,8-naphthyridine-3-carboxylate was collected, and dissolved in 30 ml of water and 20 ml of 1 N sodium hydroxide. The mixture was heated to reflux for 2 hours and acidified with acetic acid, and then adjusted to pH 8 with ammonia solution to give a precipitate. The precipitate was dissolved in diluted hydrochloric acid and adjusted again to pH 8 with ammonia water to give 1.56 g of 6-chloro-1,4-dihydro-4-oxo-7-(1-piperazinyl)-1-vinyl-1,8-naphthyridine-3-carboxylic acid, m.p. 272°–274° C.

REFERENCE 3

Preparation of a compound (compound B) of the formula;

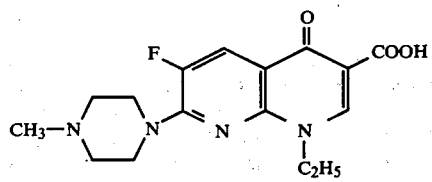

To a solution of 37% formalin (12 ml) and formic acid (18 ml) was added 6.0 g of 1-ethyl-6-fluoro-1,4-dihydro-4-oxo-7-(1-piperazinyl)-1,8-naphthyridine-3-carboxylic acid, and the mixture was heated at 120°–125° C. for 4 hours with stirring. The mixture was then concentrated to dryness under reduced pressure. The residue was adjusted to pH 8 by addition of aqueous 7% sodium bicarbonate, and extracted with chloroform. The extract was dried and the solvent was evaporated. The crystalline residue was recrystallized from a mixture of dichloromethane and ethanol to give 5.0 g of 1-ethyl-6-fluoro-1,4-dihydro-7-(4-methyl-1-piperazinyl)-4-oxo-1,8-naphthyridine-3-carboxylic acid, m.p. 228°–230° C.

COMPOUND 1

1-Ethyl-6-fluoro-1,4-dihydro-4-oxo-7-(1-piperazinyl)-1,8-naphthyridine-3-carboxylic acid

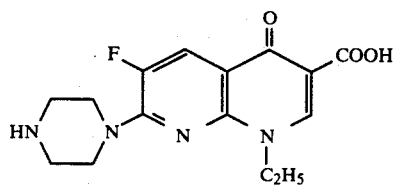

COMPOUND 1'

1-Ethyl-6-fluoro-1,4-dihydro-4-oxo-7-(1-piperazinyl)-1,8-naphthyridine-3-carboxylic acid methane sulfonate

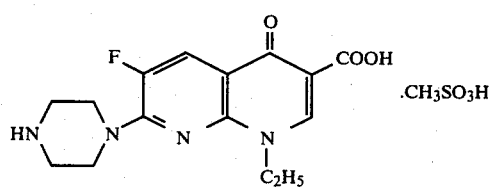

COMPOUND 2

6-Fluoro-1,4-dihydro-4-oxo-7-(1-piperazinyl)-1-vinyl-1,8-naphthyridine-3-carboxylic acid

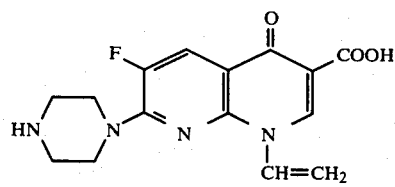

COMPOUND 3

6-Chloro-1-ethyl-1,4-dihydro-4-oxo-7-(1-piperazinyl)-1,8-naphthyridine-3-carboxylic acid hydrochloride

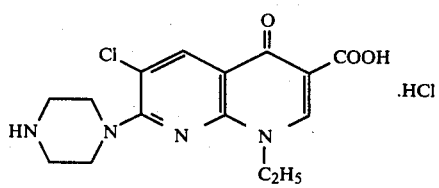

COMPOUND 4

6-Chloro-1,4-dihydro-4-oxo-7-(1-piperazinyl)-1-vinyl-1,8-naphthyridine-3-carboxylic acid

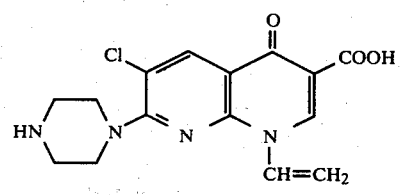

COMPOUND A

1-Ethyl-1,4-dihydro-4-oxo-7-(1-piperazinyl)-1,8-naphthyridine-3-carboxylic acid (to be sometimes referred to as 6-unsubstituted 1,8-naphthyridine)

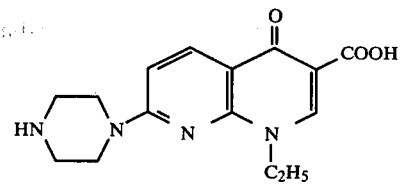

(the compound disclosed in U.S. Pat. No. 4,017,622)

COMPOUND B

1-Ethyl-6-fluoro-1,4-dihydro-7-(4-methyl-1-piperazinyl)-4-oxo-1,8-naphthyridine-3-carboxylic acid

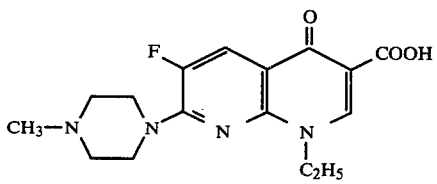

(the compound obtained by Reference 3)

COMPOUND C

6-Chloro-1-ethyl-1,4-dihydro-4-oxo-7-(1-piperazinyl)-quinoline-3-carboxylic acid

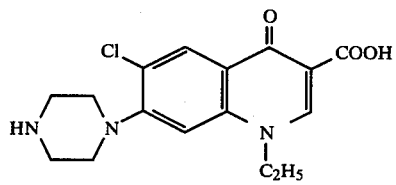

(the compound disclosed in Japanese Laid-open Patent Publication No. 65887/78)

COMPOUND D

1-Ethyl-6-fluoro-1,4-dihydro-4-oxo-7-(1-piperazinyl)-quinoline-3-carboxylic acid

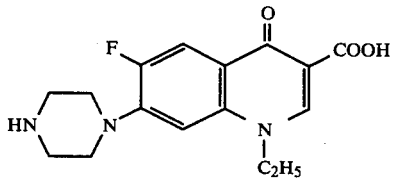

(the compound disclosed in Belgian Pat. No. 863429)

COMPOUND E

1-Ethyl-1,4-dihydro-7-methyl-4-oxo-1,8-naphthyridine-3-carboxylic acid (Nalidixic acid)

(the compound disclosed in U.S. Pat. No. 3,149,104)

COMPOUND F

8-Ethyl-5,8-dihydro-5-oxo-2-(1-piperazinyl)pyrido[2,3-d] pyrimidine-6-carboxylic acid (Pipemidic acid)

(the compound disclosed in U.S. Pat. No. 3,887,557)

COMPOUND G

α-(5-Indanyloxycarbonyl)benzylpenicillin sodium salt (Carindacillin)

(the compound disclosed in U.S. Pat. No. 3,557,090)

COMPOUND H

D-α-Aminobenzylpenicillin (Ampicillin)

(the compound disclosed in U.S. Pat. No. 2,985,648)

COMPOUND J 7-(D-α-Aminophenylacetamido)desacetoxycephalosporanic acid (Cephalexin)

(the compound disclosed in U.S. Pat. No. 3,507,861)

EXAMPLE A

The minimum inhibitory concentrations (μg/ml) in vitro are shown in Table I.

(1) Compounds 1 to 4, especially compounds 1, 1' and 2, of this invention exhibit very high antibacterial activities against Gram-positive bacteria and Gram-negative bacteria including *Pseudomonas aeruginosa*.

(2) Compound A (6-unsubstituted 1,8-naphthyridine) has much inferior antibacterial activity against Gram-positive and Gram-negative bacteria to the compounds of the present invention.

EXAMPLE B (in vivo therapeutic efficacy)

Compounds 1 to 4 and the ethyl ester of compound 1 and A to G were each dissolved in deionized water or suspended in 0.2% aqueous solution of CMC. Each of the solutions was orally administered to mice infected with each of test organisms under the conditions described below, and the median effective doses ($ED_{50}$) obtained are shown in Table II.

Experimental conditions

Mice:
Male mice (ddY) weighing about 20 g
Infection:
(1) *Staphylococcus aureus* No. 50774; Intravenous

TABLE I

In vitro antibacterial activity against 19 strains of bacteria

| Bacteria | 1 | 1' | 2 | 3 | 4 | A | B | C | D | E | F | G | H | J |
|---|---|---|---|---|---|---|---|---|---|---|---|---|---|---|
| Gram-positive bacteria | | | | | | | | | | | | | | |
| *Staphylococcus aureus* 209P JC-1 | 0.78 | 0.78 | 1.56 | 3.13 | 3.13 | 25 | 1.56 | 0.78 | 0.39 | 100 | 12.5 | 0.39 | 0.05 | 1.56 |
| *Staphylococcus aureus* No. 50774 | 0.78 | 0.78 | 3.13 | 6.25 | 6.25 | 50 | 1.56 | 1.56 | 0.78 | 50 | 25 | 0.78 | 0.1 | 1.56 |
| *Streptococcus faecalis* P-2473 | 12.5 | 12.5 | 25 | 25 | 12.5 | >100 | 12.5 | 6.25 | 3.13 | >200 | 200 | 50 | 1.56 | 200 |
| *Streptococcus pyogenes* 65A | 12.5 | 12.5 | 12.5 | 12.5 | 6.25 | 50 | 6.25 | 6.25 | — | >200 | 200 | 0.2 | 0.025 | 0.78 |
| *Corynebacterium pyogenes* C-21 | 1.56 | 1.56 | 1.56 | 6.25 | 6.25 | 50 | 1.56 | 1.56 | 0.78 | >200 | 25 | 3.13 | 1.56 | 1.56 |
| Gram-negative bacteria | | | | | | | | | | | | | | |
| *Escherichia coli* NIHJ JC-2 | 0.2 | 0.2 | 0.1 | 0.78 | 0.2 | 6.25 | 0.39 | 0.39 | 0.1 | 12.5 | 1.56 | 6.25 | 6.25 | 12.5 |
| *Escherichia coli* P-5101 | 0.1 | 0.1 | 0.05 | 0.39 | 0.1 | 3.13 | 0.2 | 0.2 | 0.05 | 3.13 | 1.56 | 6.25 | 6.25 | 12.5 |
| *Escherichia coli* P-140a | 0.2 | 0.2 | 0.1 | 0.39 | 0.1 | 6.25 | 0.39 | 0.2 | 0.1 | — | 1.56 | 50 | 200 | >200 |
| *Salmonella typhimurium* S-9 | 0.1 | 0.1 | 0.05 | 0.39 | 0.2 | 6.25 | 0.2 | 0.2 | 0.05 | 3.13 | 1.56 | 0.78 | 0.39 | 6.25 |
| *Salmonella enteritidis* No. 1891 | 0.1 | 0.1 | 0.05 | 0.39 | 0.2 | 1.56 | 0.1 | 0.2 | 0.05 | 3.13 | 1.56 | 0.78 | 0.2 | 3.13 |
| *Shigella flexneri* 2a | 0.2 | 0.2 | 0.1 | 0.78 | 0.2 | 6.25 | 0.39 | 0.39 | 0.1 | 6.25 | 3.13 | 12.5 | 3.13 | 12.5 |
| *Shigella flexneri* 4a P-330 | 0.39 | 0.39 | 0.2 | 1.56 | 0.2 | 12.5 | 0.78 | 0.2 | 0.2 | — | 1.56 | 6.25 | 6.25 | 200 |
| *Klebsiella pneumoniae* No. 13 | 0.2 | 0.2 | 0.1 | 1.56 | 0.39 | 12.5 | 0.39 | 0.78 | 0.2 | 12.5 | 6.25 | >200 | 100 | 6.25 |
| *Enterobacter cloacae* P-2540 | 0.2 | 0.2 | 0.1 | 0.78 | 0.2 | 6.25 | 0.39 | 0.2 | 0.1 | 6.25 | 1.56 | 3.13 | >200 | >200 |
| *Pseudomonas aeruginosa* Tsuchijima | 0.39 | 0.39 | 0.2 | 6.25 | 1.56 | 25 | 1.56 | 3.13 | 0.39 | 200 | 12.5 | 6.25 | >200 | >200 |
| *Pseudomonas aeruginosa* No. 12 | 0.78 | 0.78 | 0.39 | 6.25 | 1.56 | 25 | 3.13 | 3.13 | 0.78 | 200 | 25 | 50 | >200 | >200 |
| *Serratia marcescens* IFO 3736 | 0.39 | 0.39 | 0.2 | 1.56 | 0.78 | 12.5 | 1.56 | 0.78 | 0.2 | 6.25 | 3.13 | 3.13 | 25 | >200 |
| *Proteus morganii* Kono | 0.2 | 0.2 | 0.1 | 1.56 | 0.2 | 6.25 | 0.78 | 0.39 | 0.1 | 6.25 | 3.13 | 0.78 | 100 | >200 |
| *Proteus mirabilis* P-2381 | 0.39 | 0.39 | 0.2 | 3.13 | 0.78 | 25 | 1.56 | 0.39 | 0.2 | — | 3.13 | 0.78 | 3.13 | 12.5 |

Note:
The numerals in the table show minimum inhibitory concentrations (MIC) (μg/ml) Method; Chemotherapy, 22(6), 1126 (1974)

The following can be seen from the results shown in Table I.

infection with (about $5 \times 10^8$ cells/mouse) of a bacterial suspension in saline.

(2) *Escherichia coli* P-5101; Intraperitoneal infection with (about $9 \times 10^6$ cells/mouse) of a bacterial suspension in trypto-soy broth with 4% mucin.

(3) *Pseudomonas aeruginosa* No. 12; Intraperitoneal infection with 50 to 100 LD$_{50}$ (about $5 \times 10^3$ cells/mouse) of a bacterial suspension in trypto-soy broth with 4% mucin.

Medication:
Twice, about 5 minutes and 6 hours after infection.
Observation:

| | |
|---|---|
| *Staphylococcus aureus* No. 50774 | for 14 days |
| *Escherichia coli* P-5101 | for 7 days |
| *Pseudomonas aeruginosa* No. 12 | |

TABLE II in vivo Efficacy against systemic infection in mice.

| | Bacterium | | |
|---|---|---|---|
| | *Staphylococcus aureus* No 50774 | *Escherichia coli* P-5101 | *Pseudomonas aeruginosa* No. 12 |
| | | Route | |
| Compound | po | po | po |
| 1 | 10 | 1.8 | 9.0 |
| 1' | 10* | 1.8* | 9.0* |
| 2 | 33.4 | 1.3 | 2.4 |
| 3 | about 90* | 6.5* | 58.6* |
| 4 | about 100 | 4.8 | 18.5 |
| ethyl ester of 1 | about 20 | — | 21.0 |
| A | >100 | — | >200 |
| B | 4.8 | 1.2 | 10.6 |
| C | about 100 | about 15 | >100 |
| D | 21.9 | 4.7 | 15.5 |
| E | >800 | 29.2 | >200 |
| F | 215 | 21.2 | 99.5 |
| G | 10–40 | 100 | 201.6 |
| H | 2.2 | 43.5 | >400 |
| J | 12.1 | 22.6 | >400 |

Note:
The numerals in the table show ED$_{50}$ (mg/kg). ED$_{50}$ values were calculated in accordance with the Behrens-Kaerber method (Arch. Exp. Path. Pharm., 162, 480 (1931)).
po: oral administration.
*Calculated for free carboxylic acid The following conclusions can be drawn from the results shown in Table II.

(1) Compounds 1 and 1' of this invention show potent therapeutic effects on the systemic infections with Gram-positive and Gram-negative bacteria.

(2) The therapeutic effect of compound 2 of this invention against infections with Gram-positive bacteria is inferior to that of compound 1 or 1', but its therapeutic effect against infections with Gram-negative bacteria is superior. Thus, the compound 2 of the invention is especially useful for the treatment of systemic infection caused by *Pseudomonas aeruginosa*.

(3) Compounds 1, 1' and 2 of this invention exhibit better therapeutic effects against systemic infection with Gram-negative bacteria, especially *Pseudomonas aeruginosa*, than compounds A and C, compounds E and F which are commercially available synthetic antibacterial agents, and compounds G, H and J which are commercially available antibiotics.

(4) Compounds 1 and 1' of this invention are clearly superior in therapeutic effect in vivo against Gram-positive bacteria to compound D. Compounds 1, 1' and 2 of this invention are clearly better than compound D in therapeutic effect in vivo against Gram-negative bacteria including *Pseudomonas aeruginosa*.

(5) The ethyl ester of compound 1 of this invention is useful as an intermediate for the synthesis of compounds 1 and 1' of this invention. It also has superior antibacterial activity in vivo against Gram-positive bacteria and Gram-negative bacteria.

EXAMPLE C (in vivo therapeutic efficacy)

Compounds 1 and 2 and compound D were tested by the following procedure for therapeutic efficacies against the ascending kidney infection with *Pseudomonas aeruginosa* No. 12 in mice. The results obtained (ED$_{50}$: mg/kg) are shown in Table III.

Experimental method:
Female mice (ddY-S) weighing 22 to 30 g were anesthetized by intravenous injection of sodium pentobarbital at a dose of 50 mg/kg. Through a small suprapubic incision, the urinary bladder was exposed and then infected by injecting 0.1 ml of a 1:10,000 dilution of *Pseudomonas aeruginosa* No. 12 cultured for 20 hours in trypto-soy broth, using 0.25 ml syringe with 0.25 mm needle. The mice were restrained from drinking water for a period from 1 day before to 1 day after the infection and treated twice a day for 3 days starting on the day of infection. On the 5th day after infection, the kidneys were harvested for the detection of the bacteria, transversely bisected and stamped on King A Agar, which were incubated at 37° C. overnight. No bacterial finding in the kidneys was regarded as protected from the ascending kidney infection. ED$_{50}$ values were calculated by probit analysis.

TABLE III

In vivo efficacy on the ascending kidney infection with *Pseudomonas aeruginosa* No. 12 in mice

| Compound | Route | ED$_{50}$ (mg/Kg) |
|---|---|---|
| 1 | po | 2.4 |
| 2 | po | 0.56 |
| D | po | 16.1 |

From the results shown in Table III, it is seen that the therapeutic effect of compounds 1 and 2 of this invention against ascending kidney infection with *Pseudomonas aeruginosa* is clearly better than that of compound D.

EXAMPLE D (Acute toxicity)

A solution containing each of compounds 1 to 4 and compounds B to J in various concentrations was orally given to male mice (ddY) (4 to 8 in each group) at a dose of 0.1 ml per 10 g of body weight. The number of dead mice was counted after 7 days, and the value of median lethal dose (LD$_{50}$, mg/kg) was calculated in accordance with the Behrens-Kaerber method. The results are shown in Table IV.

TABLE IV

| Acute toxicity in mice. | |
|---|---|
| Compound | LD$_{50}$ (mg/kg) |
| 1 | >4000 |
| 1' | >4000* |
| 2 | >4000 |
| 3 | >2000* |

TABLE IV-continued

| Acute toxicity in mice. | |
|---|---|
| Compound | $LD_{50}$ (mg/kg) |
| 4 | >2000 |
| B | 210 |
| C | >2000 |
| D | >2000 |
| E | 1516 |
| F | >5000 |
| G | >4000 |
| H | >5000 |
| J | 3000 |

*Calculated for carboxylic acid.

The following conclusions can be drawn from the results shown in Table IV.

(1) Compounds 1 to 4 of this invention have extremely low toxicity.

(2) Compound B which results from the introduction of a methyl group into the 4-position of the 1-piperazinyl group of compound 1 of this invention shows an equivalent or higher antibacterial activity to or than the compounds of this invention as shown in Tables I and II, but has extremely high toxicity.

EXAMPLE E (Subacute toxicity)

Compound 1 was orally administered to six female mice (JCL-ICR strain) having an average body weight of 20 g at a dose of 2 g/kg once a day for 14 days. During the test period, the body weight of each mouse was measured. On the 15th day, the mice were hematologically examined. After the hematological examination, the mice were sacrificed, and the organs were weighed and histopathologically observed. Consequently, the following facts were found out.

No abnormality was observed in the group to which had been administered compound 1 of this invention with regard to body weight gain, hematological examination and histopathological observation in contrast to a control group. These demonstrate the high safety of the compound 1.

EXAMPLE F (Plasma level)

Two male Beagle dogs weighing 12 kg each were orally given a capsule containing one of compounds 1 and 2 at a dose of 25 mg/kg with 200 ml of milk respectively. Blood samples were taken by venipuncture from the two dogs at each 0.5, 1, 2, 3, 6, 8 and 10 hours after administration, and centrifuged individually to separate the plasma.

Drug levels were determined by the thin-layer cup-plate method using *Escherichia coli* Kp as an indicator organism.

The results obtained are shown in Table V.

TABLE V

| | Plasma level | | | | | | |
|---|---|---|---|---|---|---|---|
| | Time after administration (hr) | | | | | | |
| Compound | 0.5 | 1 | 2 | 3 | 6 | 8 | 10 |
| 1 | 0.6 | 2.4 | 5.5 | 5.9 | 4.2 | 3.7 | 2.4 |
| 2 | nd | nd | 1.5 | 2.8 | 5.5 | 5.2 | 4.4 |

Note:
The numerals in Table V show plasma level (μg/ml).
nd: non-detective

The following can be seen from the results shown in Table V.

(1) Compounds 1 and 2 of this invention are well absorbed in the body by oral administration, and are maintained at a high level in the plasma for a fairly long time.

Specifically, compound 1 shows a plasma level higher than the MIC values (see Table I) against most bacteria over a period of 1 to 10 hours after administration. Compound 2 shows the same plasma level over a period of at least 2 hours to even more than 10 hours after administration. For example, the plasma level (5.9 μg/ml) of compound 1 is about 8 times the MIC values against *Pseudomonas aeruginosa* No. 12 and *Staphylococcus aureus* No. 50774, and amounts to about 60 times the MIC value against *Escherichia coli* P-5101.

(2) Compounds 1 and 2 of this invention showing such a higher plasma level and a potent antibacterial activity produce superior results at low dosages in the treatment of systemic infections caused by various bacteria.

EXAMPLE G (Urinary excretion)

The urine excreted by the dogs used in Example F was pooled over a period of 24 hours, and compound 1 or 2 in the pooled urine was determined by the same method as in Example F. The results are shown in Table VI.

TABLE VI

| | Urinary excretion | |
|---|---|---|
| Compound | Concentration (μg/ml) | Recovery (%) |
| 1 | 606 | 40.7 |
| 2 | 326 | 29.4 |

The following can be seen from the results shown in Table VI.

(1) The urinary excretion of compounds 1 and 2 of this invention is fairly good, and about 30 to 40% of the compounds orally administered is excreted in the urine 24 hours later.

(2) The urinary levels (326 to 606 μg/ml) of compounds 1 and 2 amount to about 13 to 6,000 times the MIC values (0.1 to 25 μg/ml) against various bacteria as shown in Table I.

(3) Accordingly, compounds 1 and 2 of this invention exhibit superior effects at low dosages in the treatment of urinary tract infection caused by various bacteria.

As shown in Tables I to VI, the compounds of this invention, particularly compounds 1, 1' and 2 exhibit a superior therapeutic effect on the experimental infections with Gram-positive and Gram-negative bacteria and after oral administration they maintain high plasma and urinary levels for a fairly long time. Moreover, they have low toxicity. Accordingly, these compounds are effective at low dosages for the treatment of urinary tract infection and systemic infection caused by various bacteria.

In contrast, known compound A and compound C are clearly inferior in in vitro and in vivo antibacterial activities against Gram-positive and Gram-negative bacteria as shown in Tables I and II.

Compound D is clearly inferior to compounds 1, 1' and 2 of this invention in therapeutic efficacy (see Table III) against ascending kidney infection with *Pseudomonas aeruginosa*.

Nalidixic acid (compound E) and Pipemidic acid (compound F), which are commercially available synthetic antibacterial agents, and Carindacillin (compound G), Ampicillin (compound H) and Cephalexin (compound J) which are commercially available antibiotics are clearly inferior to the compounds 1, 1' and 2 of this invention in therapeutic effects (see Table II) in vivo against Gram-negative bacteria, particularly *Pseudomonas aeruginosa*.

EXAMPLE H

| Compound 1 or 2 | 250 g |
|---|---|
| Starch | 50 g |
| Lactose | 35 g |
| Talc | 15 g |

The above components were blended and granulated and filled into 1,000 capsules in accordance with conventional methods.

EXAMPLE J

| Compound 1 or 2 | 250 g |
|---|---|
| Starch | 54 g |
| Calcium carboxymethyl cellulose | 40 g |

-continued

| Microcrystalline cellulose | 50 g |
|---|---|
| Magnesium stearate | 6 g |

The above components were blended, granulated and made into tablets in a manner known per se. Thus, 1000 tablets each weighing 400 mg were formed.

What we claim is:

1. A 1,8-naphthyridine compound of the formula

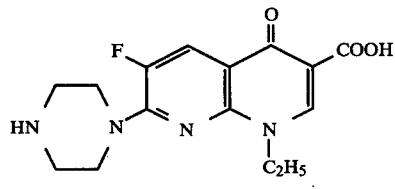

or a nontoxic pharmaceutically acceptable salt thereof.

2. A salt according to claim 1 which is a hydrochloride or methanesulfonate.

3. 1-Ethyl-6-fluoro-1,4-dihydro-4-oxo-7-(1-piperazinyl)-1,8-naphthyridine-3-carboxylic acid.

4. 1-Ethyl-6-fluoro-1,4-dihydro-4-oxo-7-(1-piperazinyl)-1,8-naphthyridine-3-carboxylic acid methanesulfonate.

* * * * *

UNITED STATES PATENT AND TRADEMARK OFFICE
CERTIFICATE OF CORRECTION

PATENT NO. : 4,359,578

DATED : November 16, 1982

INVENTOR(S) : JUN-ICHI MATSUMOTO; YOSHIYUKI TAKASE and YOSHIRO NISHIMURA

It is certified that error appears in the above-identified patent and that said Letters Patent are hereby corrected as shown below:

On the cover page of the patent, the left hand column, under "[30] Foreign Application Priority Data", change "Japan.....157939" to read --Japan.....53/157939--.

Column 7, immediately preceding line 35, insert --wherein X and $R_3$ are the same as defined above, $A^{\ominus}$ is an anion group such as a halogen atom.--.

Column 12, line 23, change "7-(4-acetyl-piperazinyl)" to read --7-(4-acetyl-1-piperazinyl)--.

Signed and Sealed this

Twelfth Day of July 1983

[SEAL]

Attest:

GERALD J. MOSSINGHOFF

Attesting Officer

Commissioner of Patents and Trademarks

UNITED STATES PATENT AND TRADEMARK OFFICE

CERTIFICATE EXTENDING PATENT TERM
UNDER 35 U.S.C. § 156

PATENT NO.: 4,359,578

DATED: November 16, 1982

INVENTORS: Jun-ichi Matsumoto et al.

PATENT OWNERS: Dainippon Pharmaceutical Co., Ltd. and Laboratoire Roger Bellon

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

2 YEARS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks